United States Patent [19]

Austin

[11] Patent Number: 5,383,475
[45] Date of Patent: Jan. 24, 1995

[54] SNORE DETERRING BELT

[76] Inventor: Ronald J. Austin, 6 Hawkridge Ave., Markham, Ontario, Canada, L3P 1V6

[21] Appl. No.: 209,715

[22] Filed: Mar. 14, 1994

[51] Int. Cl.⁶ .......................... A61F 5/56; A61F 5/37
[52] U.S. Cl. .................................. 128/848; 128/876
[58] Field of Search ............ 128/848, 875, 876, 846; 2/44, 92, 338, 310–312; 450/155

[56] References Cited

U.S. PATENT DOCUMENTS

| | | | |
|---|---|---|---|
| 663,825 | 12/1900 | Wilson | 128/871 |
| 2,304,235 | 12/1942 | Boots | 128/871 |
| 2,704,067 | 3/1955 | Moses | 602/14 |
| 2,837,088 | 6/1958 | Moses | 602/14 |
| 3,307,537 | 3/1967 | Simon | 602/8 |
| 4,958,644 | 9/1990 | Rodgers | 128/871 |

Primary Examiner—Michael A. Brown
Attorney, Agent, or Firm—David W. Wong

[57] ABSTRACT

This belt has a generally flexible portion in which several compressible wells are formed. The flexible portion is located over the back of the person wearing it around the chest. A plurality of upstanding substantially resilient semi-rigid stems are provided in the wells. The stems have a height slightly lower than the depth of the wells. When the person sleeps on the back, the weight of the body would compress the wells such that the semi-rigid stems will protrude outside of the wells to cause irritation to the back of the wearer so that the person would subconsciously turn to sleep on the side or stomach thus detering snoring to occur.

8 Claims, 2 Drawing Sheets

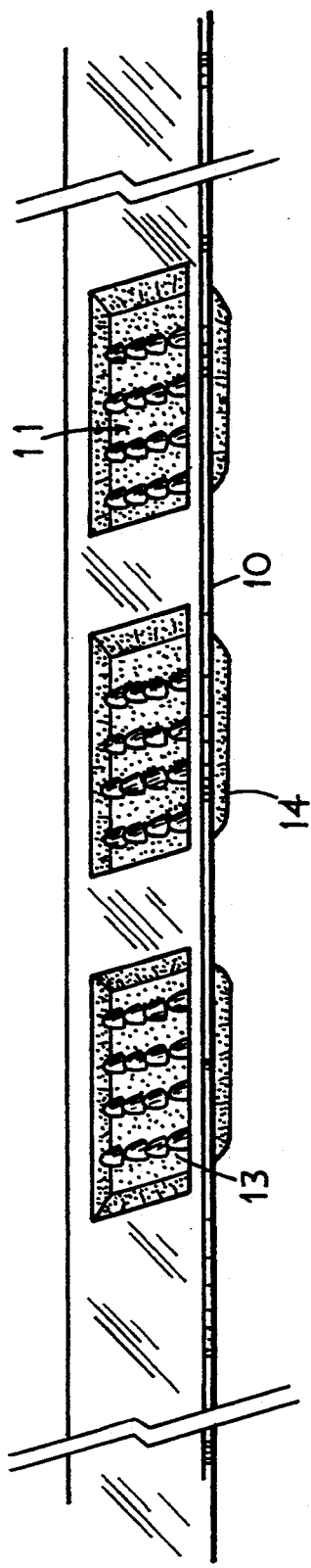
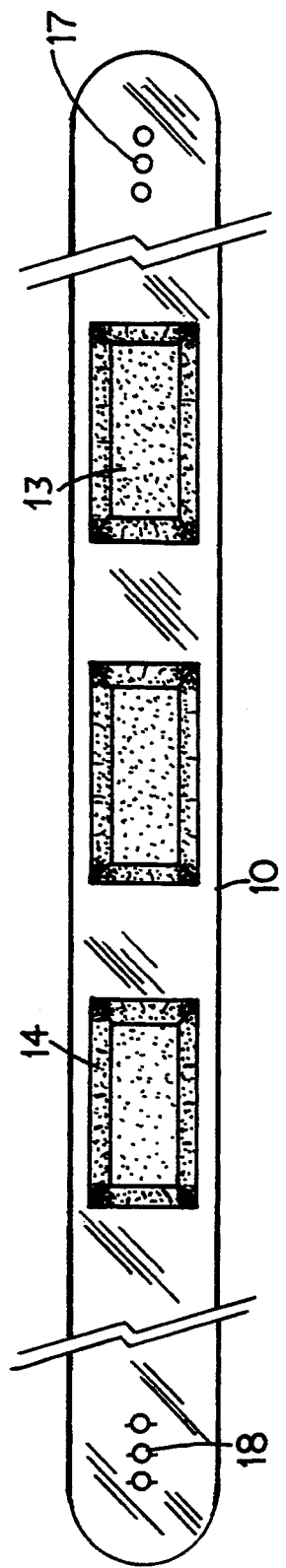

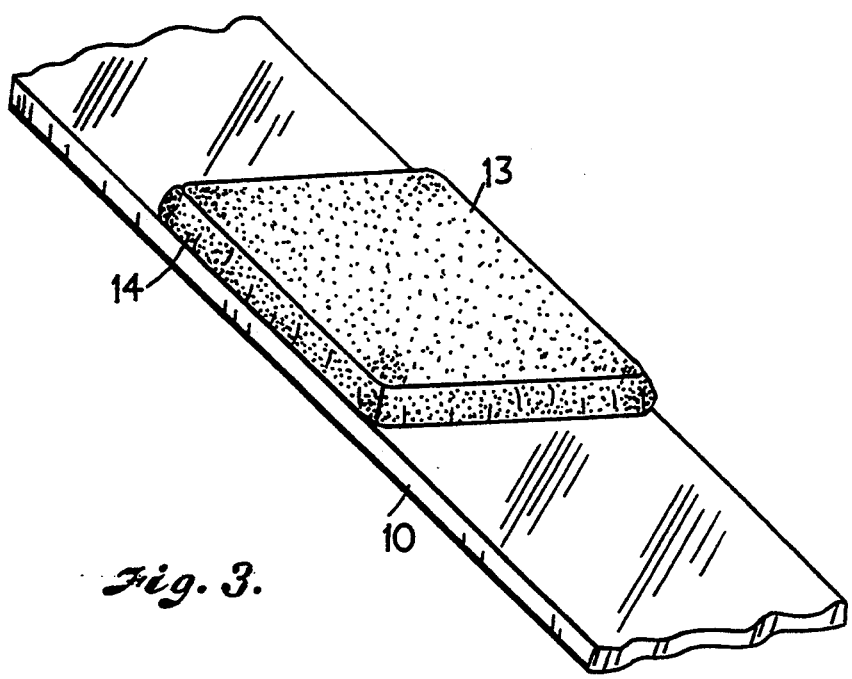
Fig. 3.
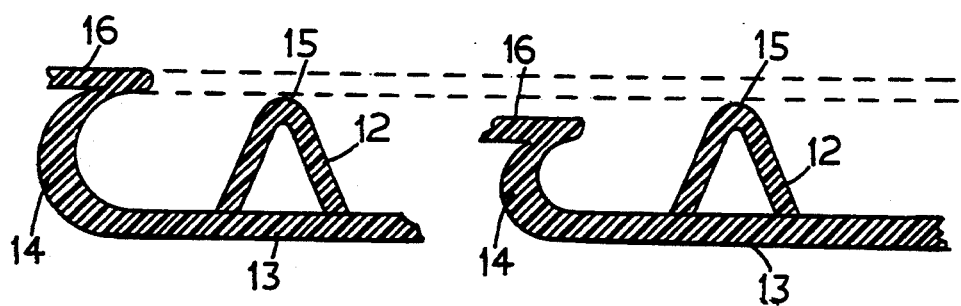
Fig. 4.   Fig. 5.
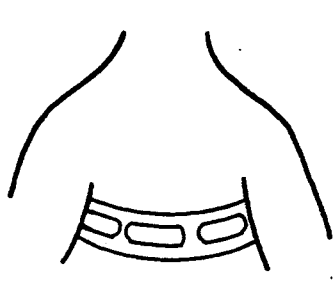   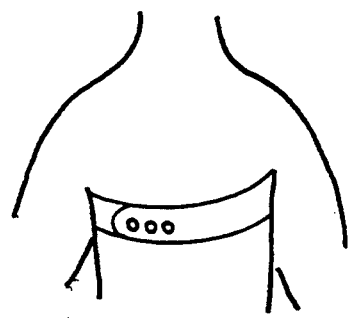
Fig. 6.   Fig. 7.

SNORE DETERRING BELT

BACKGROUND OF THE INVENTION

This invention relates to a device which can be worn by a person while sleeping to deter the person from sleeping on the back in which position snoring is prone to occur.

Snoring is widely known to occur when the person is sleeping on the back such that the soft tissue of the throat is located in a hanging position. The hanging soft tissue would vibrate in a high frequency when air passes over it in the person's breathing to produce the loud sound of snoring.

Heretofore, many devices have been developed for wearing by a person while sleeping so as to deter the person from sleeping on the back to deter snoring. Such known devices are either awkward to use or are complex in structure so that they are expensive to produce. In one construction, a plurality of balls are sewn into the back portion of a jacket which can be worn by the person. Such jacket is difficult to produce since the balls must be individually and slowly sewn into the jacket which is very time consuming to accomplish. Furthermore, such jacket is not durable and would deteriorate readily after being worn and washed several times. Also, such jacket is not effective, because if small balls are used, the profile of the balls does not cause too much irritation to the person sleeping on the back. On the other hand, if relatively large or rigid balls are used they may cause harmful effect to the person's back.

SUMMARY OF THE INVENTION

It is the principal object of the present invention to provide a belt which can be normally comfortably worn by a person sleeping and yet would cause sufficient irritation to the person's back so as to deter the person to sleep on the back.

It is another object of the present invention to provide a snore detering belt which is simple in structure.

It is another object of the present invention to provide a snore detering belt which lends itself to a mass production process.

Briefly, the belt of the present invention is to be worn by a person while sleeping for detering snoring. It comprises an elongated flexible belt member operative for being worn around the chest area of the person. A plurality of well means are formed in a substantially middle portion of the belt member. The well means are located over the back of the person wearing the belt. The well means have compressible side walls. A plurality of upstanding substantially semi-rigid cone members are formed in the well means. The cone members have a height slightly lower than the depth of the side walls of the well means.

BRIEF DESCRIPTION OF THE DRAWINGS

FIG. 1 is a top elevation perspective view of the snore detering belt according to the present invention.

FIG. 2 is a bottom elevation perspective view thereof.

FIG. 3 is an isolated bottom elevation perspective view of the well formed in the belt.

FIG. 4 is a side isolated cross sectional view of the well and the stem therein in the normal condition.

FIG. 5 is a side isolated cross sectional view of the well in the compressed condition with the stem therein protruding outwards of the well.

FIG. 6 is a perspective rear view of the person's back with the snore detering belt worn thereon.

FIG. 7 is a perspective front view of the person's front with the snore detering belt worn thereon.

DETAILED DESCRIPTION OF THE PREFERRED EMBODIMENTS

With reference to the drawings in which like reference numerals designate like parts in the several views, the snore prevention belt 10 of the present invention has a flexible belt structure which may be made of a mouldable plastic material. A plurality of wells 11 are formed in the generally middle portion of the belt 10. A plurality of upstanding substantially resilient and semi-rigid stems or cones 12 are provided on the base 13 of each well 11 and extending outwards towards the opening of the well. The stems or cones 12 have a height slightly lower than the depth of the side walls 14 of the well 11. The side walls 14 preferably have a curved profile as best shown in FIG. 4 so as to enhance their compressibility and durability.

The wells 11 and the stems or cones 12 may be integrally moulded or formed in the belt 10, and the stems or cones 12 may be hollow or solid in structure. The stems or cones 12 have a generally cone shape with a substantially rounded top end 15. In the normal condition, the top end 15 of the stems or cones 12 is located just below the top edge 16 of the well 11 as shown in FIG. 4. When the well 11 is in the compressed condition, the top end 15 of the stems or cones 12 will extend outside of the top edge 16 of the well as best shown in FIG. 5.

The belt 10 may be worn by the person around the chest while sleeping as shown in FIGS. 6 and 7 with the provision of buckle means, or pins 17 with a larger head and mating openings 18 or Velcro (trade mark) fastening means. The wells 11 are positioned over the back area of the person as shown in FIG. 6 when the belt 10 is worn.

When the person turns to sleep on the back, the weight of the body will compress the wells 11 such as to cause the stems or cones 12 to protrude outside beyond the top edge 16 of the sdie walls 14 of the wells 11 to cause irritation to the wearer's back such that the person would subconsciously turn to sleep on the side thus detering snoring.

Additionally various shapes of heads may be provided on the top end of the stems or cones 12 to provide selected irritation effects. Furthermore, the side walls 14 may have a larger thickness in order to increase their durability.

Obviously, numerous modifications and variations of the present invention are possible in light of the above teachings. It is therefore to be understood that within the scope of the appended claims, the invention may be practised otherwise than as specifically described herein.

What is claimed is:

1. A belt to be worn by a person while sleeping for deterring snoring, comprising
    an elongated flexible belt member operative for being worn around the chest area of the person, said belt member being moulded of a plastic material,
    a plurality of well means integrally formed in a substantially middle portion of said belt member, said well means being located in a single row over said middle portion and being located over the back of the person wearing said belt member, said well means having compressible side walls, a plurality of upstanding substantially semi-rigid cone members integrally formed in a base portion of each of said well means, said cone members having a height slightly lower than the depth of the side walls of said well means when said side walls are in a normal uncompressed state.

2. A belt according to claim 1 including fastening means provided at end portions of said belt member and being operative for maintaining said belt around the chest area of the person.

3. A belt according to claim 1 wherein said cone members have a solid structure.

4. A belt according to claim 1 wherein said cone members have a hollow structure.

5. A belt according to claim 1 wherein said cone members have a rounded top end.

6. A belt according to claim 5 including a selected head member provided on said top end of said cone members.

7. A belt adapted for being worn by a person while sleeping for deterring snoring, comprising an elongated single flexible belt member operative for being worn around the chest area of the person, said belt member being moulded of a plastic material, a plurality of well means formed in a substantially middle portion of said belt member, said well means extending in a single row over said middle portion and being located over the back of the person wearing said belt member, said well means having compressible side walls and a generally flat base, a plurality of upstanding compressible semi-rigid cone members integrally formed on said base and extending normally to a height just below the top edge of said side walls when said side walls are in a normal uncompressed state.

8. A belt according to claim 7 including fastening means provided at two end portions of said belt member and operative for maintaining said belt mounted around the chest area of the person.

* * * * *